United States Patent
Cole et al.

(10) Patent No.: US 7,051,012 B2
(45) Date of Patent: May 23, 2006

(54) USER INTERFACE SYSTEM FOR MAINTAINING ORGANIZATION RELATED INFORMATION FOR USE IN SUPPORTING ORGANIZATION OPERATION

(75) Inventors: Douglas J. Cole, Valley Forge, PA (US); Mike Digiacomo, Douglasville, PA (US); Ilene Sue Yost, Collegeville, PA (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 569 days.

(21) Appl. No.: 10/167,288

(22) Filed: Jun. 11, 2002

(65) Prior Publication Data

US 2003/0076342 A1    Apr. 24, 2003

Related U.S. Application Data

(60) Provisional application No. 60/337,840, filed on Oct. 22, 2001.

(51) Int. Cl.
  *G06F 17/30* (2006.01)
(52) U.S. Cl. .............................................. 707/2; 705/4
(58) Field of Classification Search .................... 707/2; 705/4

See application file for complete search history.

(56) References Cited

U.S. PATENT DOCUMENTS

| | | | |
|---|---|---|---|
| 5,957,520 A * | 9/1999 | Suda et al. .................... 706/54 |
| 5,999,908 A * | 12/1999 | Abelow .......................... 705/1 |
| 6,055,506 A * | 4/2000 | Frasca, Jr. ...................... 705/3 |
| 6,061,057 A * | 5/2000 | Knowlton et al. .......... 715/744 |
| 6,067,548 A | 5/2000 | Cheng ........................ 707/103 |
| 6,072,493 A | 6/2000 | Driskell et al. ............. 345/356 |
| 6,101,479 A * | 8/2000 | Shaw ............................. 705/8 |
| 6,185,576 B1 * | 2/2001 | McIntosh ..................... 707/200 |
| 6,311,192 B1 | 10/2001 | Rosenthal et al. .......... 707/200 |
| 6,341,267 B1 * | 1/2002 | Taub ............................ 705/11 |
| 6,356,899 B1 * | 3/2002 | Chakrabarti et al. ............ 707/5 |
| 6,366,909 B1 * | 4/2002 | Yuasa et al. .................... 707/4 |
| 6,632,251 B1 * | 10/2003 | Rutten et al. ............... 715/530 |
| 6,697,783 B1 * | 2/2004 | Brinkman et al. ............. 705/3 |
| 6,735,569 B1 * | 5/2004 | Wizig ............................. 705/4 |
| 2001/0037227 A1 | 11/2001 | McInnis et al. ................ 705/7 |
| 2001/0051879 A1 * | 12/2001 | Johnson et al. ................ 705/2 |
| 2002/0004727 A1 * | 1/2002 | Knaus et al. ................... 705/3 |
| 2002/0013716 A1 * | 1/2002 | Dunham et al. ............... 705/2 |

(Continued)

OTHER PUBLICATIONS

Signature Product Description Information Jun. 1985.

(Continued)

*Primary Examiner*—Wayne Amsbury
(74) *Attorney, Agent, or Firm*—Alexander J. Burke

(57) ABSTRACT

A system and user friendly display interface supports creation and modification of a flexible and comprehensive organization structure model able to support provision of clinical care, patient tracking, billing and administration. A method provides a user interface for maintaining organization related information in support of organization operation. The method involves receiving search criteria for use in identifying organization characteristic information. The search criteria is employed in searching a profile comprising information identifying an encompassing organization structure including information identifying multiple constituent organizations and associated organization type and user determinable organization role. Search result information is processed in providing organization characteristic information suitable for presentation to a user via a displayed image in response to user command. A user interface menu supports modification of information representing the encompassing organization structure by adding, removing or moving an organization in the encompassing organization structure and updating a database to incorporate the modifications.

14 Claims, 11 Drawing Sheets

U.S. PATENT DOCUMENTS

| | | | |
|---|---|---|---|
| 2002/0018066 A1 | 2/2002 | Vizer | 345/428 |
| 2002/0023006 A1 | 2/2002 | Partos et al. | 705/26 |
| 2002/0032740 A1 | 3/2002 | Stern et al. | 709/206 |
| 2002/0035593 A1 | 3/2002 | Salim et al. | 709/202 |
| 2002/0052928 A1 | 5/2002 | Stern et al. | 709/218 |
| 2002/0059201 A1 | 5/2002 | Work | 707/3 |
| 2002/0059251 A1 | 5/2002 | Stern et al. | 707/10 |
| 2002/0059253 A1 | 5/2002 | Albazz et al. | 707/10 |
| 2002/0059484 A1 | 5/2002 | Matsuzuki | 710/5 |
| 2002/0082464 A1* | 6/2002 | Japp et al. | 600/10 |
| 2002/0128879 A1* | 9/2002 | Spears | 705/4 |
| 2002/0138301 A1* | 9/2002 | Karras et al. | 705/2 |
| 2003/0009357 A1* | 1/2003 | Pish | 705/4 |

OTHER PUBLICATIONS

Structuring the Observatory Data, System Guide for Administrators pp. 53-54.

Health Supplier http://www.healthtrade.com.tw/en/left/healthsupplier-en.htm.

*Organization Profile* (*OP Form*) http://www.unece.org/ceiproj/ex1op.htm.

MyDocOnline http://www.mydoconline.com/MDLProduct/views/PhysicianContactForm.jsp.

* cited by examiner

Find a Health Provider Organization (HPO)

Search by:

Name: W — ☐ Exact match

Role: ☐ Encounter Provider  ☑ Service Provider  ☐ Receivable Owner

Type of HPO:

Status: Preliminary

Encounter location:

Results: (45 found - you might want to narrow your criteria)

| HPO name | Type | Status |
|---|---|---|
| Wayne Cardiology Group | Physician office | Preliminary |
| Wayne Childrens Hospital | IP Hospital | Preliminary |
| Wayne Family Medicine | Clinic | Preliminary |
| Wayne Family Practice | Physician office | Preliminary |
| Wayne General Hospital | IP Hospital | Preliminary |
| Wayne GH Emergency | ER | Preliminary |
| Wayne Medical Associates | Physician office | Preliminary |
| Wayne Physical Therapy | Ancillary | Preliminary |
| Wayne Medical Specialists | Physician office | Preliminary |
| Wayne Rehabilitation Ctr | Ancillary | Preliminary |
| Women's Assoc for Health | Physician office | Preliminary |
| Women's Clinic | Clinic | Preliminary |
| Women's Health Group | Physician office | Preliminary |
| Women's Healthcare | Physician office | Preliminary |
| Women's Medical Center | Clinic | Preliminary |

Details:
Wayne Medical Specialists
Role(s): RO SP EP II EM
<Main contact shipping address>
Encounter locations: <location 1>, <location 2>, <location 3>

[Go search]  [Clear search]  [OK]  [Cancel]

FIG. 11

USER INTERFACE SYSTEM FOR MAINTAINING ORGANIZATION RELATED INFORMATION FOR USE IN SUPPORTING ORGANIZATION OPERATION

This is a non-provisional application of provisional application Ser. No. 60/337,840 by D. J. Cole et al. filed Oct. 22, 2001. This application is concurrently filed together with commonly owned related application entitled, A System for Maintaining Organization Related Information for Use in Supporting Organization Operation, Ser. No. 10/167,730 filed Jun. 11, 2002.

FIELD OF THE INVENTION

This invention concerns a system and user interface for processing organization related information for use in supporting healthcare or other organization operation, for example.

BACKGROUND OF THE INVENTION

Modern healthcare requires the provision of services to patients by many health-care workers at a multiplicity of locations and involves a corresponding multiplicity of organizations (e.g. companies, payers, institutions, physician practices, clinics, hospitals, pharmacies etc.). Healthcare operations are structured into specialized departments such as nursing, laboratory, radiology, pharmacy, surgery, emergency, administrative and other departments which are variously located at one or more sites and may be associated with different organizations. The management of organization information involves accumulating, processing and maintaining large quantities of information. This information is employed in determining organizational relationships, affiliations and characteristics used in creating a representative organizational model supporting provision of clinical care, patient tracking, billing and administration and other purposes. Consequently, there is a need for a computerized system capable of defining and maintaining organization information for a health care enterprise and for supporting healthcare system operation by defining, processing and filtering organization information for presentation to users and other system software applications.

Available organization information management systems have limited capabilities and numerous deficiencies. Specifically, available systems are typically restricted in organization structure models that are supported. Available systems also have a limited capability to identify and define and model specific organization characteristics and structures. One known system provides a fixed hierarchical organization structure of seven levels including: a healthcare enterprise, a billing organization, a billing office, clinics and departments, a specialty, a reserved level and providers. These levels are constrained to be identified when the associated model structure is created. Further, the defined hierarchical organization model is limited in its ability to support billing administration for entities at the different levels (e.g. for different organization healthcare reimbursement plan groups at different levels of the structure).

Other limitations of the known system include an inability to accommodate types of organizational relationships. These include, for example, relationships among organizations external to a billing function and other loose affiliations within a health system (encompassing a service provider not affiliated with the health system, but required for use by the patient's payer, for example). Further, limitations include lack of search and reporting capability and inability to portray an organizational structure in a user selectable hierarchical, flat or other format. Other available organization information system deficiencies include an inflexible interface for updating and maintaining an organization profile that typically requires off-line system re-programming. In consequence it is desirable to provide an organization information system that is robust, flexible, comprehensive and user-friendly. A system according to invention principles addresses the identified deficiencies and derivative problems.

SUMMARY OF THE INVENTION

A system and user friendly display interface supports creation and modification of a flexible and comprehensive organization structure model able to support provision of clinical care, patient tracking, billing and administration. A method provides a user interface for maintaining organization related information in support of organization operation. The method involves receiving search criteria for use in identifying organization characteristic information. The search criteria is employed in searching a profile comprising information identifying an encompassing organization structure including information identifying multiple constituent organizations and associated organization type and user determinable organization role. Search result information is processed in providing organization characteristic information suitable for presentation to a user via a displayed image in response to user command.

BRIEF DESCRIPTION OF THE DRAWING

FIG. 11 shows a composite user interface display image including a first window supporting a user search for an organization within a particular organization structure model and a second window showing corresponding search results, according to invention principles.

DETAILED DESCRIPTION OF INVENTION

Figure 1:
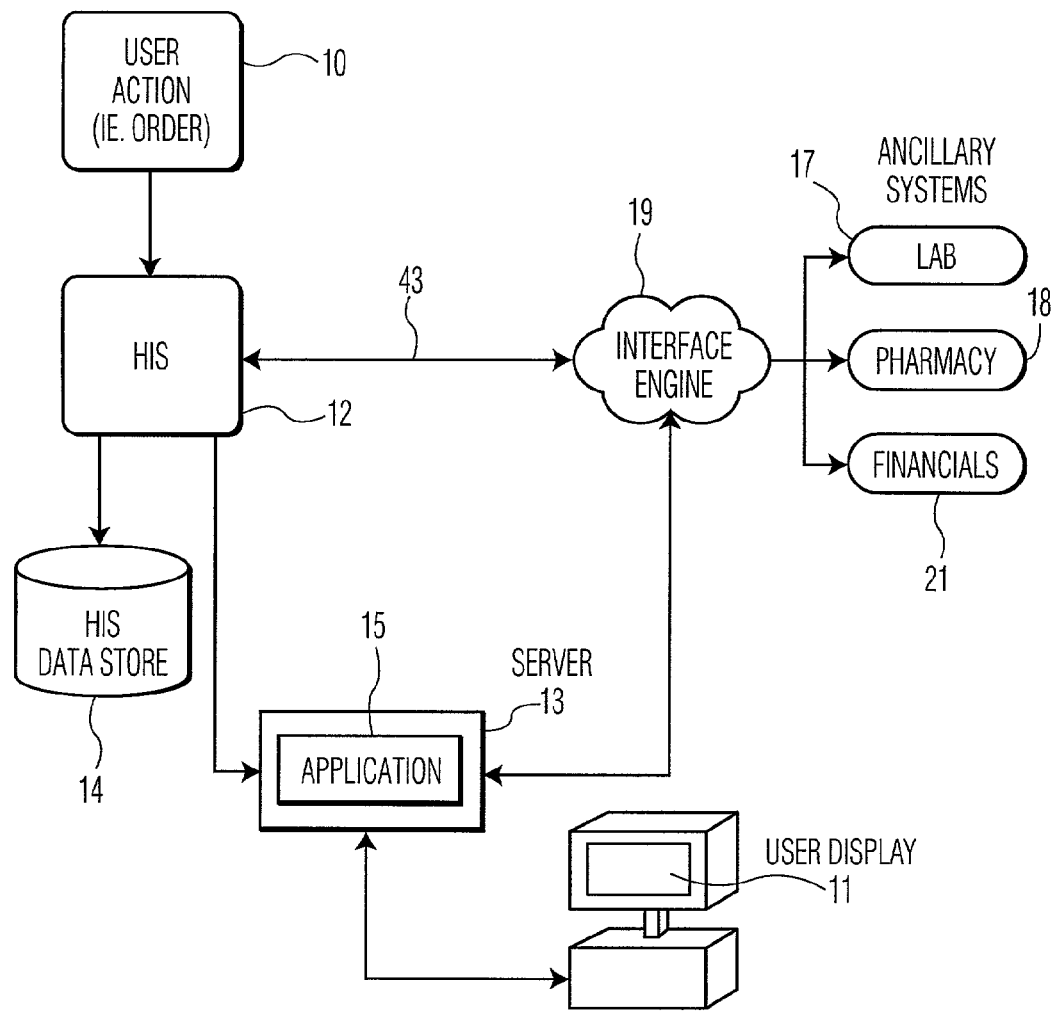
FIG. 1 shows a healthcare enterprise employing an organization management information system, according to invention principles.

FIG. 1 shows a healthcare enterprise employing an organization management information system. The organization management information system supports creation, management and modification of a profile comprising information identifying a hierarchical organization of constituent organizations associated with healthcare delivery. Although, the embodiments are described in the context of healthcare associated organizations, this is exemplary only. The principles of the invention are readily applicable to any form of hierarchically structured organization. Further, as used herein, an organization comprises a grouping of entities or an individual entity such as an institution, an enterprise, a company, a department, a government, an operation, a corporation, a clinic, an office, a business, or sub-units within them. The organization management information system enables maintenance of organization related information to support operational processes such as billing and accounts receivable, and to facilitate access to appropriate organizations and associated information. The system facilitates setup and minimizes user maintenance of an organizational hierarchy used to support organizational operational system functions and to streamline healthcare system workflow. Workflow as used herein comprises a sequence of tasks or operations that are scheduled for performance, or are being performed, by one or more entities including individuals, groups of individuals, or personnel assigned to perform particular functions or roles.

The organizations defined may comprise a Health Provider Organization (HPO) or organizations that directly or indirectly provide health related services within an Integrated Health System (IHS). An organization management information profile is contained in a master file. Further, the profile information is collated for presentation in different structural presentations. The organization information may be selectively presented in a hierarchical or non-hierarchical type presentation. Specifically, a hierarchical structured information presentation is used to represent a billing structure of an IHS, to indicate a particular HPO that manages the billing and accounts receivable for multiple HPOs providing services. Also a non-hierarchical structured information presentation is used to indicate HPOs that are not part of an operational hierarchy, for example.

An organization management information system facilitates collation and presentation of organization information of a particular profile in a hierarchical or other arrangement that supports the financial operation and business processing of a health system. The profile incorporates organizational characteristics including roles, contact information, data indicating relationships with other organizations, and membership identification. The system supports search for organization information based on multiple criteria or conditions and facilitates profile maintenance to reflect organizational or situational changes. Specifically, the systems allows a search to be entered (e.g., using partial legal or alias organization name) to find multiple HPOs for modification of their characteristics, for example. The system further enables a profile or portion of a profile to be replicated and used as the basis for a new profile and allows an inactive preliminary profile to be created ready to be activated upon a change in organizational structure. A profile may also be time and date stamped and an obsolete profile may be stored to support tracking of organizational changes for billing and other purposes. An organization may be dynamically added to a profile during an operational activity such as during a patient registration and a profile may also encompass organizations that are not directly affiliated with a health system but provide an ancillary service, for example.

In the FIG. 1 healthcare enterprise, an organization management information system is embodied in application 15 executing on server 13 and accessed by remote PC and associated user interface 11. The location management information system bidirectionally communicates with Healthcare Information System (HIS) 12 employing patient record repository 14 in processing user actions 10 such as treatment related orders including medication preparation orders, for example. In addition, organization management application 15 and HIS 12 bidirectionally communicate with external systems 17–21 through an interface engine 19. Interface engine 19 may comprise a workflow processing application or other application supporting communication with external systems 17–21. External systems 17–21 comprise a laboratory 17, pharmacy 18 and financial application (such as for patient service tracking and billing) 21, for example, but may also encompass a broader range of systems including any system with which HIS 12 performs a transaction or data exchange. Further Healthcare Information System (HIS) 12 may comprise other types of information system such as a Clinical Information System or Critical Care Information System or another Information system. In other embodiments organization management application 15 may reside in other types of enterprise including non-healthcare information systems involving organization management for tracking people goods or services.

Figure 2:
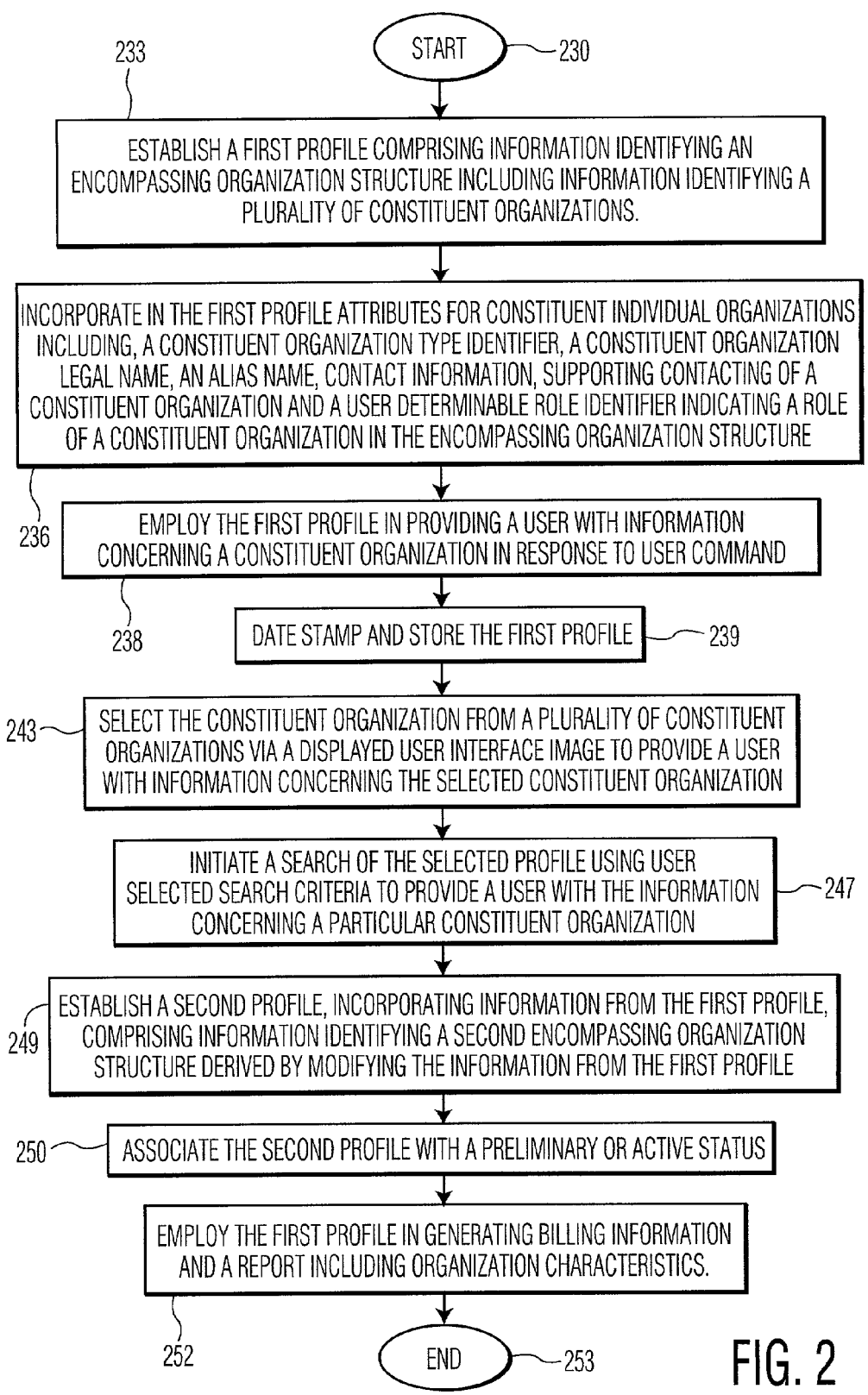
FIG. 2 shows a flowchart of a process employed by the organization management information system of FIG. 1 in presenting searching and processing organization information, according to invention principles.

FIG. 2 shows a flowchart of a process employed by the organization management application 15 of FIG. 1 in creating, maintaining, searching, processing and presenting organization information in response to user command. In step 233 after the start at step 230, application 15 supports user creation and maintenance of a first profile comprising information identifying an encompassing organization structure and constituent organizations. The organization first profile may be freshly created or may be derived by editing an existing profile stored in a master file. Application 15 supports the following profile creation and editing functions for this purpose.

I. Define organizations to the system
   A) Define organizational characteristics
      1. Identify organization types
         a) Health provider
            System provides ability to define relationships with individual health professionals associated with an organization
            System provides ability to define relationships with the locations where an organization provides services
            System provides ability to define relationship with services provided by an organization
         b) Payer
            System provides ability to define various health plan product offerings
            System provides ability to define customized group offerings of health plan products System provides ability to define rules for management of health care services (coverage and reimbursement) at a health plan or group plan level System provides ability to create or remove links to health plans from a payer's contact list System provides ability to dynamically create or update organization information during patient processing such as during check in or other process c) Business office
 d) Administrative
  System provides ability to define organizations that do not play a direct health providing role within a health enterprise but play an ancillary role in system processing (e.g. organizations that issue identifiers to people or other organizations, or employers)
2. Identify organization basic characteristics
 a) Legal Name
 b) Alias Names
3. Identify roles, relationships and status
 a) Roles for any organization type
  Employer/sponsor
  Identifier Issue
  Guarantor
 b) Roles for a Health Provider organization type
  Employer/sponsor
  Identifier Issue
  Guarantor
  Receivable owner
  Service provider
  Encounter provider
 c) Relationships
  Associate Health Professionals with Service Providers
  Associate Receivable owner and Business Office
  Associate Service Provider and Encounter Location
  Associate Service Provider and Services
4. Identify contact information
 a) System provides ability to determine contact use
  Main contact
 b) System provides ability to define contact type. At least one of the following is defined for each contact: contact name, address, phone numbers and email address. The following template starter set contact types are provided:
  Claim Submission
  Claim Inquiry
  Benefits Inquiry
  Authorization
  Contract Negotiation/Renegotiations
  Contract Stop Loss Billing
  Contract Stop Loss Follow Up
  Employment—Worker's Comp
  Payments/Remittance
  Billing/Account Inquiry
  Billing Inquiry—Provider
  Contract Negotiation
  Guarantor Billing Information Inquiry
  Guarantor Billing Submission
 c) Support for user defined qualifier such as "sick out of area"

II. Define hierarchical structure
 A. Hierarchical maintenance functions to facilitate creation and maintenance of organization structure
  Edit tree details
  Validate tree
  Delete a preliminary tree
  Select an HPO node
  Edit node (HPO) details
  Remove node from tree
  Add node to tree
  Move node within tree
III. Search organization information
 A. Use multi-select or single-select find dialog
  1. Use one or more of the following criteria to search for or filter any organization type:
   a) Organization type
   b) Organization role
   c) Organization name(s)—legal or alias
   d) Organization identifier(s)
   e) Employer reporting significance
   f) Employer reporting group
   g) Contact city
   h) Contact state
   i) Identifier definition type
  2 Use one or more of the following criteria to search for or filter any Health Provider Organization:
   a) HPO type
   b) HPO status
   c) Service provider list indicator
   d) Service provider encounter location
   e) Encounter location—current, past, future In response to user command, application 15 uses its profile creation and editing functions in step 236 (FIG. 2) to incorporate in the profile attributes for constituent individual organizations including, an organization type identifier, a user determinable role identifier indicating a role of a constituent organization in the encompassing organization structure, a legal name, an alias name and contact information. The organization type identifier identifies whether an organization is a health care provider organization, a health care payer organization, a health care administration organization or a business organization, for example. The role identifier identifies whether an organization acts as, an employer, an issuer of identifiers for identifying items associated with a person, a payment guarantor, a creditor, a service provider or as a host of a patient encounter with a healthcare enterprise. An encounter as used herein comprises any event involving patient and healthcare enterprise interaction (e.g. patient visit, phone call, inpatient stay, examination, consultation, tests etc.). The role identifier also identifies an organizational relationship such as a relationship between an individual involved in health care delivery and a health care service provider, a relationship between a creditor and a business organization or a relationship between a health care service provider and an organization including a location for hosting a patient encounter. The constituent organization contact information includes contact name, contact address, contact phone number or contact Email address. The constituent organization contact information includes a template set of contact types prompting contact information to be incorporated for authorization, claim submission or inquiry, billing, benefits inquiry, contract information or guarantor information. Further, application 15 advantageously supports user selection of a role identifier of a constituent organization via a displayed user interface image without requiring reprogramming of executable code to implement a new role. The created profile is used by application 15 in step 238 (FIG. 2) to provide a user with information concerning a constituent organization.

In step 239 in response to user command, application 15 validates and date and time stamps the created first profile for storage in a database. For this purpose application 15 applies predetermined rules in validating the created (or modified) organization profile. The first profile is time and date stamped to indicate a first date the first profile is valid and a last date at which the profile is valid. The date and time stamping of an organization structure profile advantageously enables tracking of patient charges for constituent organizations and verification of billing information. In step 243, application 15 selects a constituent organization from multiple constituent organizations within the first profile in response to user selection via a displayed user interface image. Application 15 in step 247 searches the first profile using user selected search criteria to provide a user with information concerning the constituent organization selected in step 243. The search criteria may include one or more of, a portion or whole organization legal name, a portion or whole organization alias name, organization type, organization role, organization identifier, employer information, contact information or service provider information.

In step 249 in response to user command, application 15 establishes a second profile identifying a second encompassing organization structure incorporating information from the first profile created in step 233 and derived by user modification of the first profile. Application 15 associates the second profile with a user determinable preliminary status or active status indicator in step 250. The second profile is time, date stamped and stored in similar fashion to the first profile. In step 252 application 15 employs the second profile in finding information concerning a particular organization and in generating a report including organization characteristics and in generating billing information in response to user entered search criteria. The process of FIG. 2 terminates at step 253.

Figure 3:
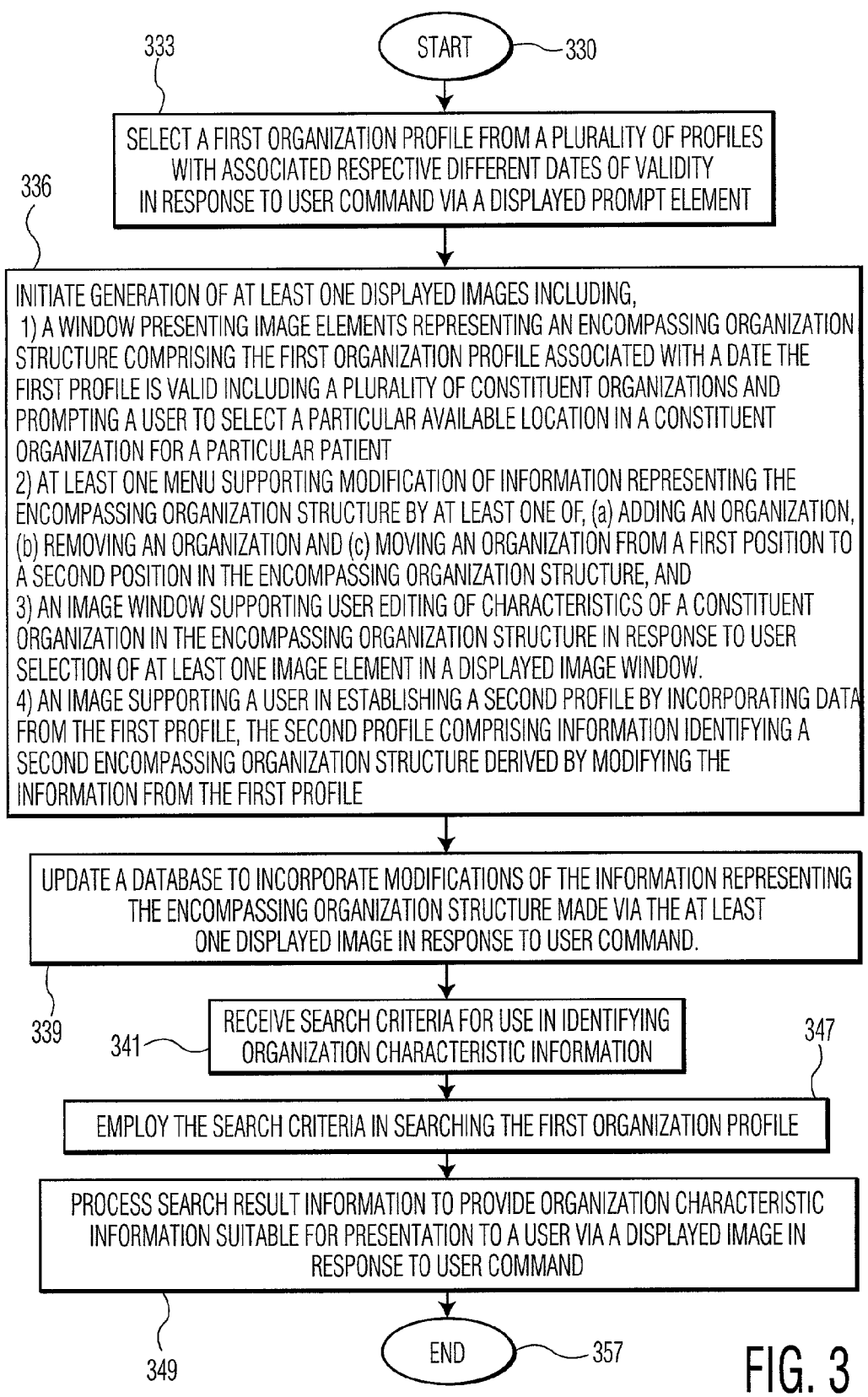
FIG. 3 shows a flowchart of a process for creating, modifying and maintaining an organization profile within the organization management information system of FIG. 1, according to invention principles.

FIG. 3 shows a flowchart of a process for creating, modifying and maintaining an organization profile within the organization management information system of FIG. 1. In step 333 after the start at step 330, in response to user command application 15 selects a first organization profile from multiple organization profiles with associated dates of validity via a displayed user interface image. In step 336 application 15 initiates generation of one or more displayed images including a window presenting image elements representing an encompassing organization structure of the selected first profile including multiple constituent organizations. The window includes a display element prompting a user to select a particular available location for a particular patient in a constituent organization of the first organization profile. Application 15 also initiates generation of one or more displayed menus supporting modification of information representing the encompassing organization structure. Such modification includes, adding an organization, removing an organization and moving an organization from a first position to a second position in an encompassing organization structure. Application 15 also initiates generation of an image window supporting user editing of characteristics of a constituent organization in response to user selection of at least one image element in the displayed image window. Application 15 also initiates generation of one or more displayed images supporting a user in establishing a second profile identifying a second encompassing organization structure by incorporating data from the first profile.

Figure 4:
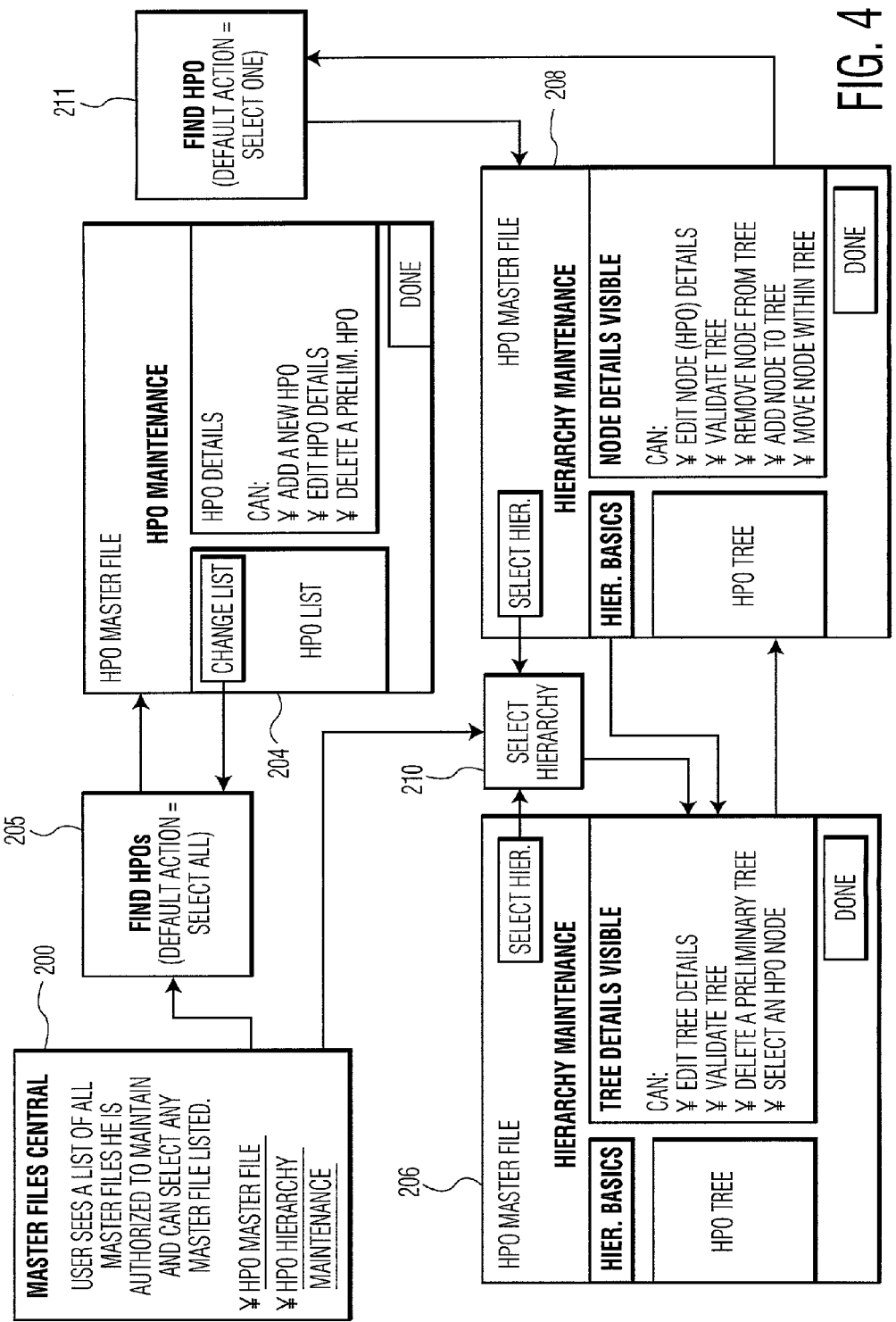
FIG. 4 shows a user interface display image navigation sequence supporting the organization management information system, according to invention principles.

FIG. 4 shows a user interface display image navigation sequence supporting editing of an organization profile in step 336 of FIG. 3. In response to user command, display image 200 of FIG. 4 is presented showing a list of master files containing data representing corresponding organization profiles. Display image 200 includes at least one prompt element supporting user selection of a profile from multiple profiles with associated respective different dates of validity. Display image 200 is used to initiate creation and maintenance of a hierarchical organization profile (via display images 206 and 208) or maintenance of organization characteristics (via display image 204). A user may select (via image 200) an organization profile master file in step 210 (FIG. 4) for viewing, editing and validation of an organization hierarchical tree and associated tree details (e.g., for directly editing tree details) via display image 206. Similarly, a user may select (via image 200) an organization profile master file in step 210 (FIG. 4) for viewing, editing and validation of a particular node (organization representative item) and associated node characteristics within a hierarchical organization tree (e.g., for removing or adding a node) via display image 208. Display image 208 also supports finding an organization and associated node characteristics for viewing and editing in command step 211. In addition, image 200 supports finding a particular organization or multiple organizations associated with a particular profile (step 205) for viewing and editing of characteristics of individual organizations (e.g., for adding or deleting details of a particular organization such as services associated with the particular organization) via display image 204.

Figure 6:
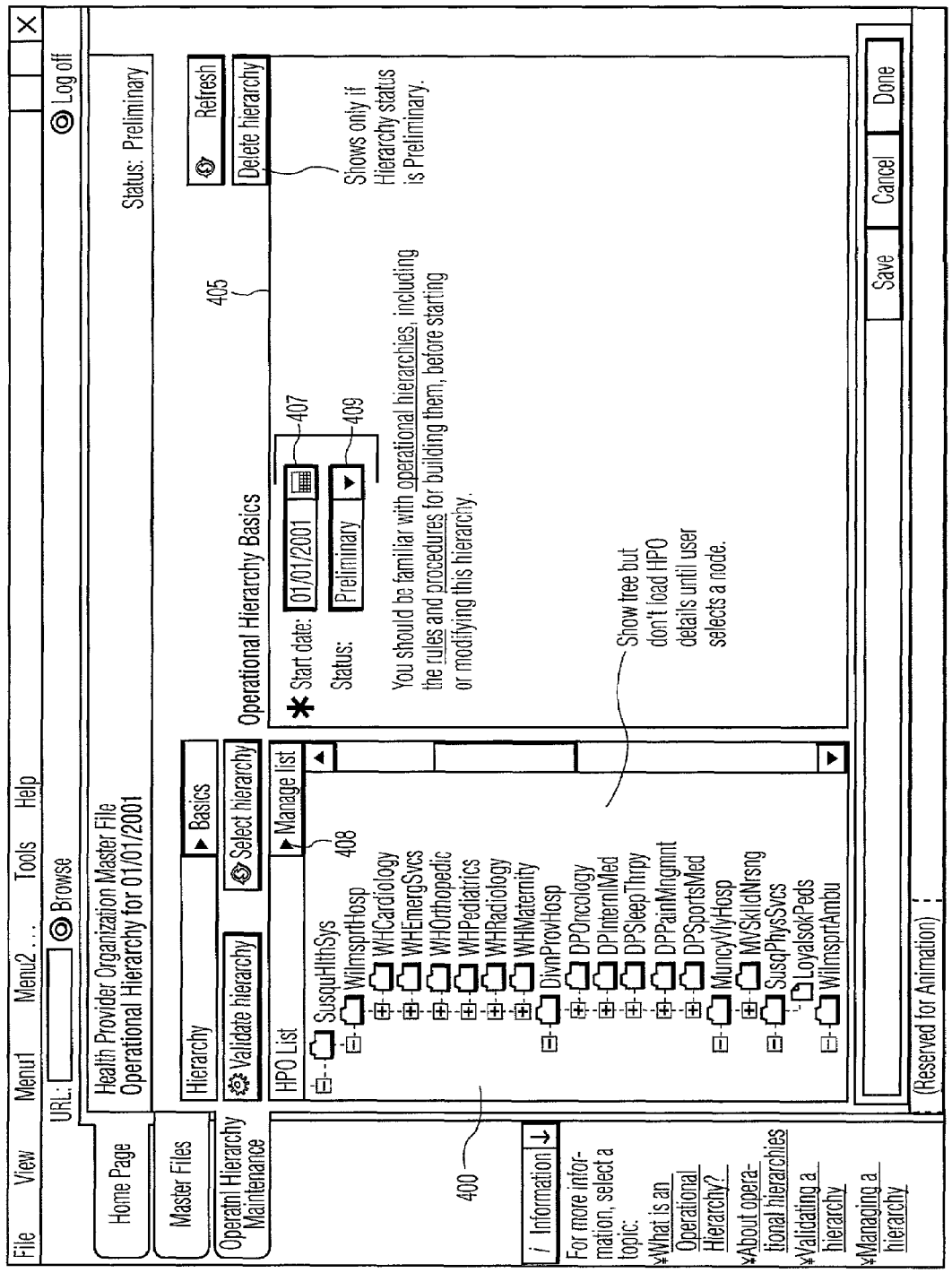
FIG. 6 shows a user interface display image supporting maintenance of an organization structure model, according to invention principles.

FIG. 6 shows a user interface display image for use in maintaining a organization profile of the type employed in display images 206 and 208 of FIG. 4, for example. The display image of FIG. 6 includes windows 400 and 405. Window 400 is used to indicate a currently selected hierarchical organization profile structure in a tree format representation. Window 405 is used for showing characteristics of items selected in window 400 and for initiating editing and validation operations on the selected organization profile or its selected items. Item 407 of window 405 indicates the currently selected organization profile is valid from start date Jan. 1, 2001, for example. Item 409 indicates the currently selected organization profile is of preliminary status and inactive.

The FIG. 6 image is displayed in response to user selection of an organization hierarchy maintenance item (e.g., within image 200 of FIG. 4). In the absence of an existing organization profile the FIG. 6 image display opens in an add mode presenting a blank node in window 400 with an edit cursor in start date field 407. A user accepts a default date (equal to current date plus one day) or enters a new date in item 407. A hierarchy status defaults to preliminary status and may not be changed until at least one node is entered. A user initiates creation of an organization profile by selecting icon 408. If the FIG. 6 image display opens in response to selection of an existing organization profile the structure of the profile is shown in window 400. For this to occur the organization items comprising the profile hierarchy need to be already defined. Application 15 validates a created preliminary profile to prevent creation of multiple preliminary profiles of the same type with the same date. Multiple concurrent profiles of the same type and date but of different status (e.g., one preliminary and one active) are permitted.

A preliminary or active profile may be copied and used as the basis for modification and creation of a new profile which is given an initial default preliminary status. An item is added to a preliminary profile by selecting an existing item in a hierarchy and indicating whether a new item is to be inserted above, below, or at the same level as the selected item. A blank item is inserted at the desired point and a prompt is generated prompting a user to find an item for insertion. If a desired item is found, it is inserted to replace the blank item. If a desired item is not found a user may elect to add a new item (e.g., an organization or other item) via an organization or hierarchy profile maintenance menu (e.g. via display images 204, 206 or 208 of FIG. 4). Further, a preliminary hierarchy is validated in response to user command or automatically upon activation when a user makes a preliminary hierarchy active.

Returning to the flowchart of FIG. 3, application 15 in step 336 and in response to user command also initiates generation of displayed images (such as images 204, 206 or 208 of FIG. 4). Such displayed images include menus supporting modification of information representing the first organization profile to derive a second profile representing a second organization structure encompassing multiple constituent organizations. The menus support adding an organization, removing an organization, moving an organization from a first position to a second position in the hierarchical organization of organizations, editing characteristics of organizations and validating an edited profile. In step 339, application 15 updates a database to incorporate data representing the second profile derived by modifying information representing the first profile.

Application 15, employs user entered search criteria received in step 341 in searching a database storing information representing the first profile in step 347 to determine organization characteristics. In step 349 application 15 processes derived search result data to provide organization characteristic information to a user via a displayed image. The process of FIG. 3 ends at step 357.

Figure 5:
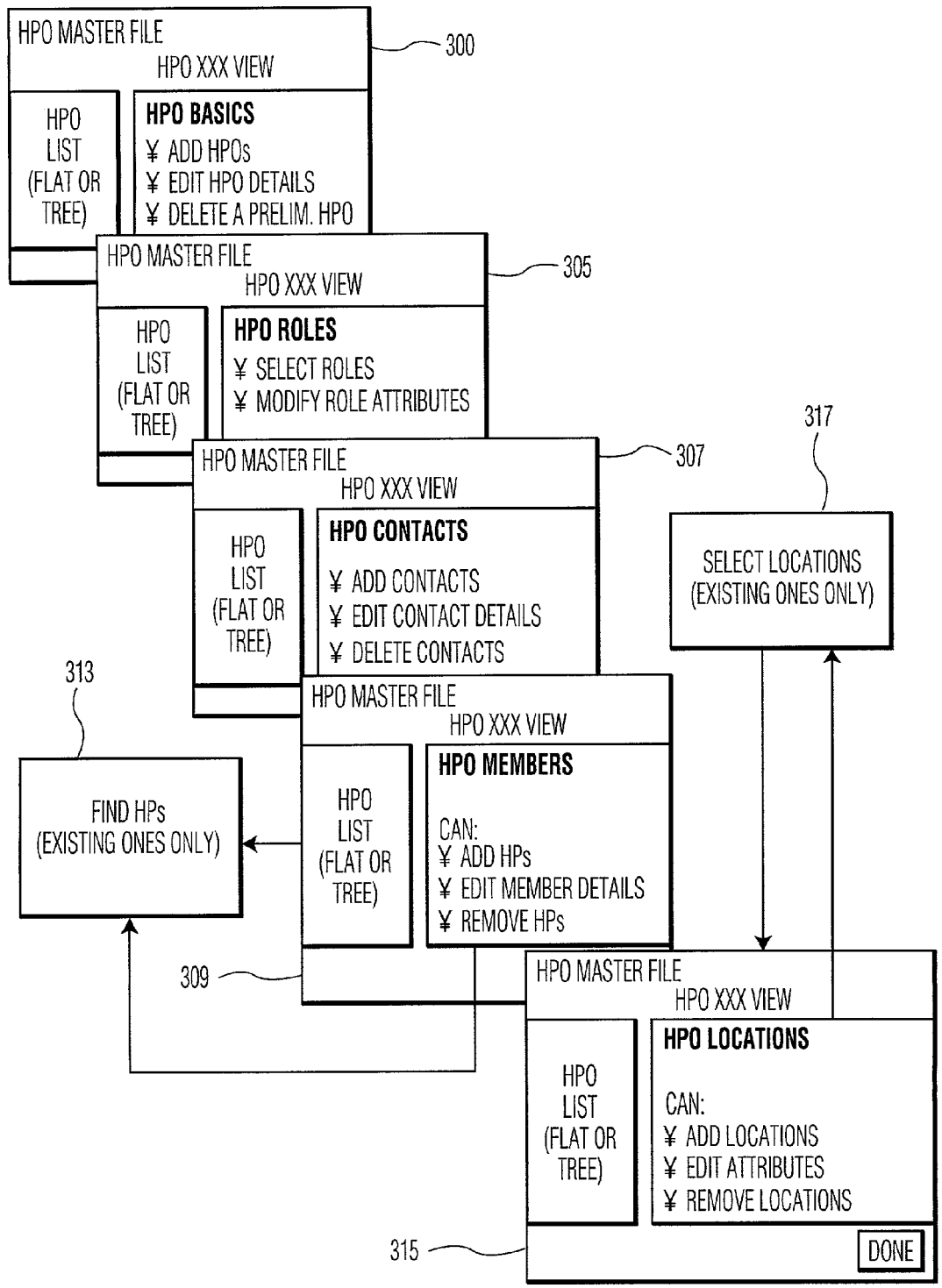
FIG. 5 shows a user interface display image navigation sequence supporting maintenance of an organization structure model, according to invention principles.

FIG. 5 shows a user interface display image navigation sequence supporting maintenance of an organization structure model. In response to user command, application 15 initiates generation of a display image presenting a user selected organization profile master file 300. Display image 300 (and subsequent images in the FIG. 5 sequence) provides a currently selected hierarchical (tree or flat view) organization profile structure representation in one window and a second window supporting profile amendment. Specifically, a window in image 300 supports user addition or deletion of an organization in the current profile or editing of characteristics of an organization in the current profile. A user also determines organization type via image 300. Specifically, four different and mutually exclusive types of organization may be designated. A single organization may not be more than one of these types but an organization type may be changed. The four types of organization involved are detailed as follows.

1. Health Provider Organization (HPO)—these are the organizations that either directly provide health services to consumers or are the parent entities of organizations that directly provide services to consumers. An HPO has the following characteristics:
    Ability to define various health plan product offerings.
    Ability to define customized group offerings of the health plan products.
    Ability to define rules for the management of health care services (coverage and reimbursement) at the health plan or group plan level.
    Ability to create or remove links to health plans from contact information of a particular payer
    Dynamic establishment of payer information through Patient Management processes such as patient registration.
2. Payer Organization—these are organizations that pay for or underwrite coverage for health services through health plan product offerings. The health plans include specific sets of benefits that are available to the public either through direct subscription or as sponsored group plans offered by organizations such as employers or membership organizations. A payer may be a governmental agency, a non-profit organization, a commercial insurance company, a Managed Care Organization, or some other organization.
3. Business Office—these are organizations that perform or manage the billing and collection responsibilities of an HPO or a collection agency.
4. Administrative Organization—these are organizations that play a role within an encompassing organization, but are not direct participants in the delivery of health services (e.g. employer/sponsors, issuers of identifiers).

A user also determines organization characteristics via image 300 including demographic information, reporting names as well as associations an organization has with other entities, such as contacts or health plans. In particular, an organization may have a Legal name and an Alias name. A Legal name is a name that an organization uses for official communication. An Alias name is any other name that an organization is known by. Application 15 employs rules, as follows, in processing Legal and Alias name information.

Legal name processing rules:
    Legal name is required to create an organization.
    One legal name is permitted per organization.
    An organization's legal name may not be deleted
    A history of legal names for an organization is usually not maintained.
    Legal names may be used for searching organizations.
Alias name processing rules:
    Alias processing is typically used for searching organizations.
    There may be multiple aliases for an organization.
    A history of alias names is usually not maintained.
    An incorrect alias may be deleted or replaced.
    An alias may be added to an organization with no restrictions.
    An alias can be used as a desired reporting name.

Image 305 is initiated in response to a user command via image 300 and includes a window supporting addition, deletion or editing of patient organization role information in the current profile. The organization types play various roles within a system. Some organization roles are common to multiple types of organizations, while others are specific to individual types of organizations. The following roles apply to organization types:
    Employer/Sponsor—The Employer/Sponsor represents the organizations that people within a system are employed by. They are associated with incidents (e.g. a work related accident) or named as guarantors for patient encounters. Organizations in the role of employer/sponsor are eligible to be organizational guarantors.
    Identifier issuer—The Identifier issuer issues identifiers for other organizations or people (health professionals and persons).
    Guarantor Roles that are health provider organization type specific include:
    Receivable Owner—A Receivable Owner owns the money for services rendered by it or a subordinate organization.
    Service Provider—A service provider "performs" and "offers"services. A Service Provider either has its own catalog of services ("service catalog") that it provides or potentially shares a "service catalog" with other Service Providers.

Encounter Provider—An Encounter Provider is responsible for "hosting Encounters" and checking patients into and out of encounters. An Encounter Provider initiates generation of a user interface used for patient management (and scheduling) activities pertaining to encounters that are hosted by the Encounter Provider.

The following relationships are defined between organizations:

Relationships between Service Providers and Health Professionals

Relationships between Receivable Owner and Business Office

The hierarchy also supports the definition of relationships between Service Providers and Encounter Locations.

An organization may issue identifiers for people, other organizations or objects (e.g. encounters). Application 15 supports user determination of the types of identifiers that an organization may issue, (an HPO may be determined as being able to issue Medical Record Numbers, for example). Thereby a user may also search for organizations that issued particular identifiers. Further, an organization is able to delegate an identifier issuing function to another organization and application 15 supports user indication of those specific identifier types that an organization is designated to issue. As an example, an Integrated Health Network (IHN) is delegated to issue medical record numbers for the hospitals in its network but each hospital issues its own encounter numbers.

An organization that is determined to be an employer is eligible to become an organizational guarantor. An organizational guarantor is designated for various reasons, including, for example:

Drug testing required by an employer—the employer is the guarantor

A prisoner who is currently incarcerated—the prison is the guarantor

Situations involving liability, where the patient or family is not to be billed—the insured party responsible for injury expenses may be the guarantor, i.e., the employer in the case of worker compensation In these situations application 15 enables an organization to be designated as a responsible party for any balance remaining after insurance coverage. Further, an organization may be identified as a guarantor during a patient management function, such as patient registration, for example.

An organization may play a role of guarantor, employer, and identifier issuer and an organization profile is altered in accordance with predetermined rules in response to user activation or inactivation of particular roles of an organization. There is no restriction for making an organization an employer. There is also no restriction for making an organization an identifier issuer. An organization may be designated as an identifier issuer with associated identifier issuance capabilities. Once activated, an employer and identifier issuer role may not be inactivated except under the limited circumstance of there being no designated identifier issuance capabilities associated with the organization concerned.

Application 15 supports designation of a particular organization type to perform a particular role. A Healthcare Provider Organization (HPO), for example, may be designated as a service provider by user command upon a certain condition. Specifically, application 15 examines active profile hierarchies that an HPO appears in and verifies that the HPO includes a valid receivable owner constituent organization in each of the active profile hierarchies. If the HPO does not include a valid receivable owner in any of the profile hierarchies, application 15 generates an error message to a user indicating that the HPO may not be made a service provider. An HPO designated as a service provider is included in associated organization search results unless the user indicates the HPO is not to be included in such search results. Once an HPO is designated as a service provider it may not be inactivated as a service provider, however application 15 may designate that the HPO is not to appear on a list of valid service providers. This prevents users from being able to select the HPO as a service provider using the profile.

Application 15 supports designation of an HPO as an encounter provider and designates an encounter provider as a service provider. Further, application 15 allows entry of a start date and termination date at which an HPO began or stopped admitting patients as an encounter provider, or as a default selection, application 15 assumes an HPO has always acted as an encounter provider. Once an HPO is designated as an encounter provider it may not be inactivated as an encounter provider, however application 15 may designate that the HPO is not to appear on a list of valid encounter providers. This prevents users from being able to select the HPO as an encounter provider using the profile. Further, application 15 supports designation of an HPO to act in a Receivable Owner role and creates a Participating Provider role for the HPO. This role is used by the system internally for self pay Receivable Units or whenever participation in a health plan group, for example, has not been defined.

In FIG. 5, image 307 (generated in response to a user command via image 305), includes a window supporting addition, deletion or edit of organization contact information (e.g., organization address information) in the current profile. Organization contact data provides information on where or how to contact an organization for a reason termed a useType. The organization contact information is comprised of at least one of the following: address, phone number, e-mail address, or a contact name and is established when an organization profile is created or following its creation. A useType is determined based on business characteristics and reflect the way an organization performs specific business processes. For example, Payer organizations have useTypes such as Main contact, Insurance Claim Submission contact, Claim Inquiry contact, Benefit Inquiry contact, etc.

A constituent organization contact information includes a template set of contact types prompting contact information to be incorporated as follows.

Template Contact useTypes include the following:

Main ("Main" is used as a general purpose contact for an organization).

Claim Submission—These contacts are used in the submission and acceptance of claims from an HPO Claim Inquiry—These contacts are used to inquire on claims status and denial issues.

Benefits Inquiry

Authorization—These contacts are used for scheduling and/or Registration to get authorizations and/or pre-certifications.

Contract Negotiation/Renegotiations

Contract Stop Loss Billing

Contract Stop Loss Follow Up

Employment—Worker Compensation

Payments/Remittance—These contacts are used by cashiers, cash control staff or manager to inquire about payments and remittance information.

Billing/Account Inquiry

Billing Inquiry—Provider

Contract Negotiation

Guarantor Billing Information Inquiry—These contacts are used to interrogate an organizational guarantor on bill status and denial issues.

Guarantor Billing Submission—These contacts are used in the submission and acceptance of bills to a guarantor from an HPO In addition to useType, a qualifier is used to further narrow the intention of the contact. Examples of qualifiers include indicators identifying, geographical area (such as PA—Eastern), Mental/Substance Abuse, Rebill/Supplemental Claim, Admission, Pre-Cert/Registration, Referral from a primary care physician and Sick-Out-Of-Area.

Health provider organization members are added, edited or removed in a window in image 309 presented in response to user command via image 307. For this purpose, health provider organizations may be selected via generation of a search image (step 313) in response to user command via image 309. Similarly health provider organization locations are added, edited or removed in a window in image 315 presented in response to user command via image 309. For this purpose, health provider organization locations may be selected for editing via generation of a location selection image (step 317) in response to user command via image 315.

Figure 7:
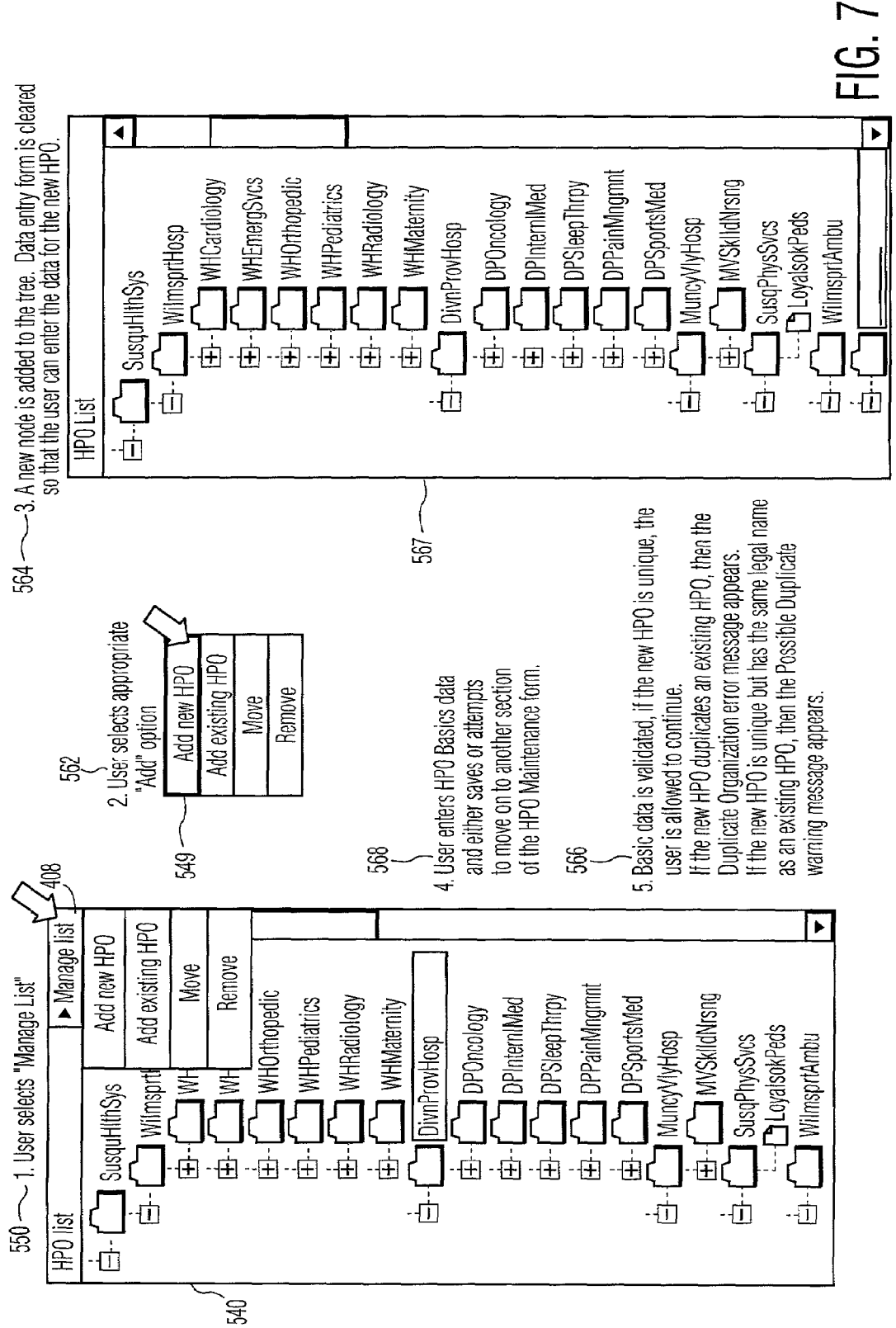
FIG. 7 shows a user interface display image navigation sequence supporting adding a new organization node to a particular organization structure model, according to invention principles.

FIG. 7 shows a user interface display image navigation sequence supporting addition of a new organization node to a particular organization structure profile model. In FIG. 7, a user adds a new HPO to an existing profile hierarchy. In order to do this, a user selects manage list item 408 in step 550 (e.g. from within display image 300 of FIG. 5) and selects add option 549 in step 562 from within a resulting prompt action list. Application 15 adds a new node representing the HPO in step 564. The added node is shown in window 567 with an item label ready for name data entry. A user in step 568 enters data and characteristics concerning the added HPO and in step 566 application 15 validates the entered characteristics and determines whether the added HPO is a duplicate of an existing HPO in the profile. Application 15 in step 566 also initiates generation of a message indicating an added HPO is a duplicate or is a possible duplicate or has a duplicate name.

Figure 8:
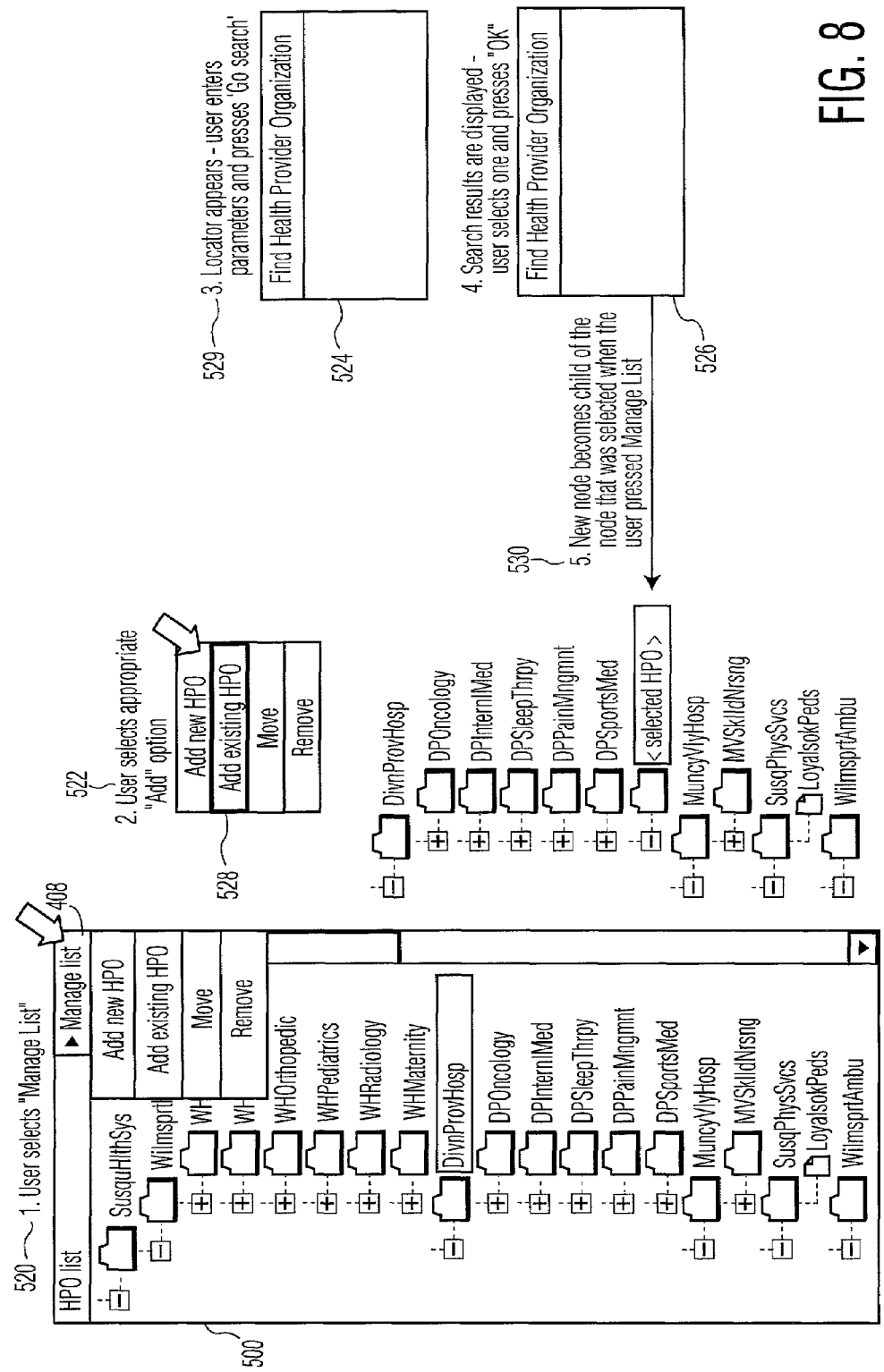
FIG. 8 shows a user interface display image navigation sequence supporting adding an already created organization node to a particular organization structure model, according to invention principles.

FIG. 8 shows a user interface display image navigation sequence supporting adding an already created organization node to a particular organization structure model. In FIG. 8, a user selects an organization in window 500 to be a parent organization of a (previously created) HPO. For this purpose, a user selects manage list item 408 in step 520 (e.g. from within display image 300 of FIG. 5) and selects add option 528 (for adding an already existing organization) in step 522 from within a resulting prompt action list. In response, application 15 generates search window 524 in step 529 and upon user entry of search parameters and initiating a search via window 524, application 15 displays search results in window 526. Following user selection of an HPO from the displayed HPO list in search result window 526, application 15 in step 530 adds a node representing the selected HPO to the previously selected parent organization in window 500.

Figure 9:
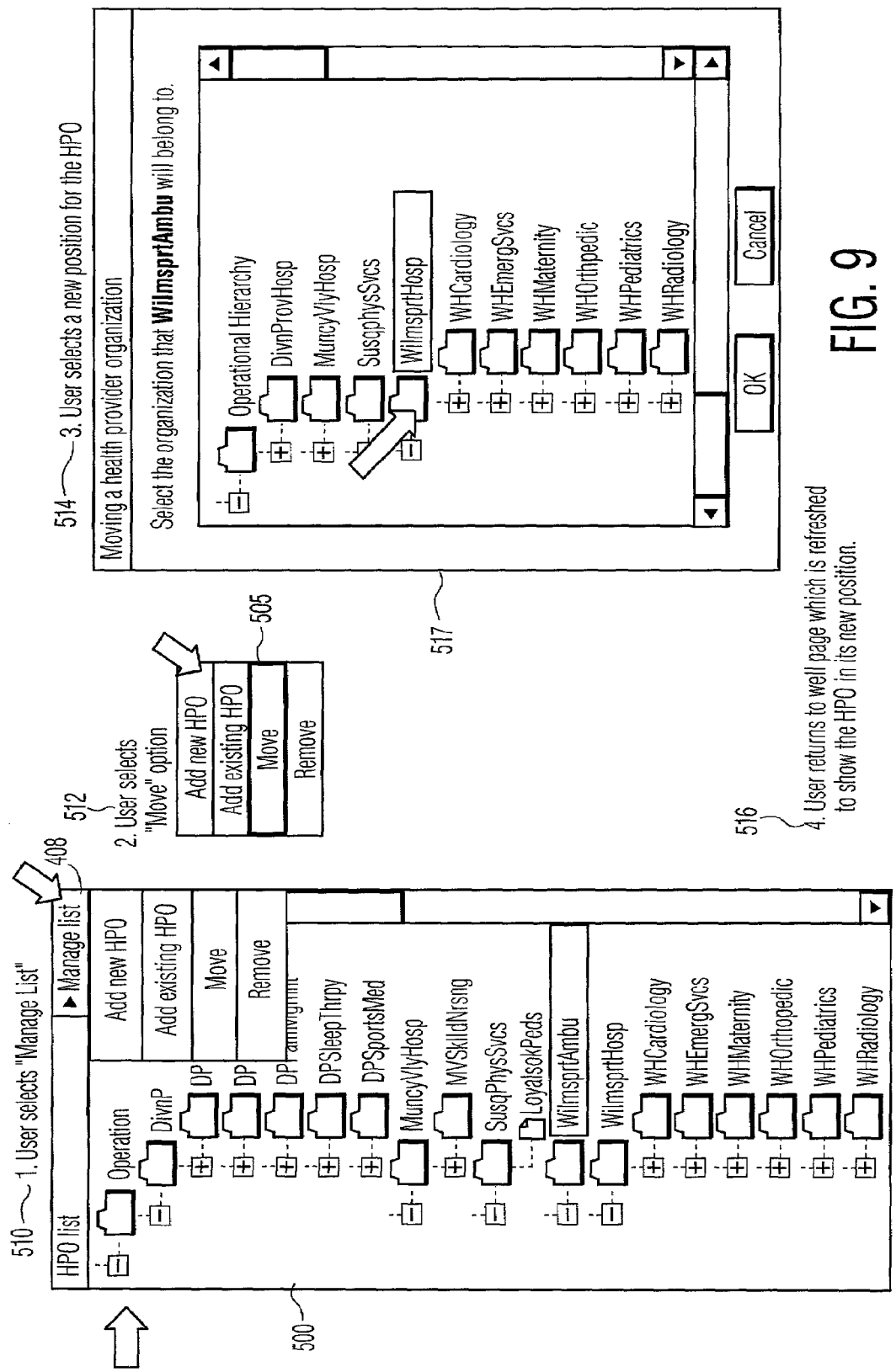
FIG. 9 shows a user interface display image navigation sequence supporting moving an organization node within a particular organization structure model, according to invention principles.

FIG. 9 shows a user interface display image navigation sequence supporting moving an organization node within a particular organization structure model. In FIG. 9 a user moves an existing item in a current profile to another point within the same location profile hierarchy (e.g., WilmsprtAmbu to WilmsprtHosp—in window 500) by selecting the organization item (WilmsprtAmbu) to be moved in window 500. A user selects manage list item 408 in step 510 (e.g. from within display image 300 of FIG. 5) and selects move option 505 in step 512 from within a resulting prompt action list. The user selects another existing item in window 517 (generated in step 514) to be used as a destination item (WilmsprtHosp in window 517). The user further indicates if the item is to be inserted above, below, or at the same level as the destination item (WilmsprtHosp). Application 15 initiates generation of a message identifying an item is to be moved as well as its intended destination and if the user confirms acceptance of the move, it is completed, and the resulting new hierarchy is displayed in step 516. If the user does not confirm acceptance, the hierarchy is left unchanged. A user follows a similar procedure in using manage list item 408 and a resulting prompt action list (step 512) to remove an organization. Application 15 initiates generation of a message indicating that the item and its subordinates are to be permanently removed from the hierarchy and a user confirms or rejects acceptance in the manner described for moving an existing item.

Figure 10:
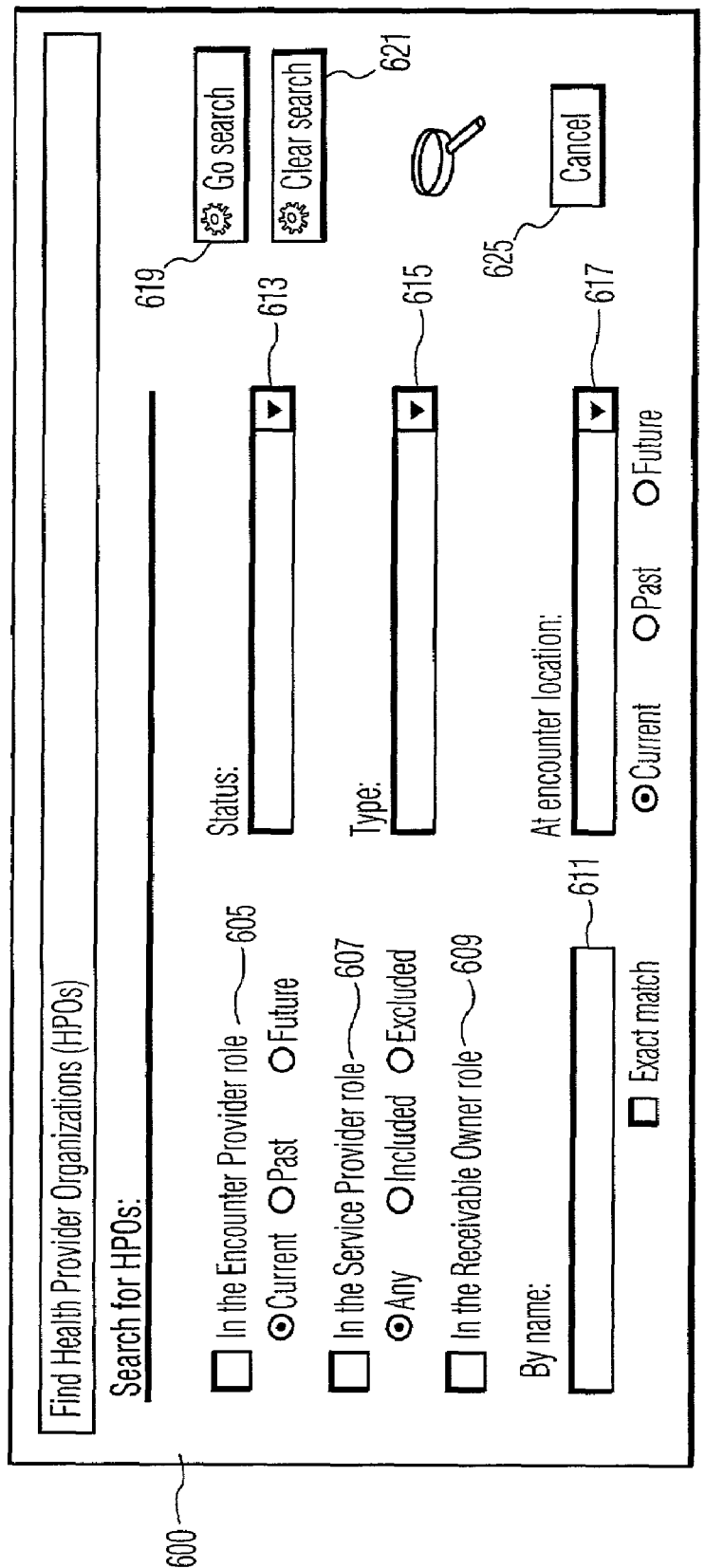
FIG. 10 shows a user interface display image menu supporting a user search for an organization within a particular organization structure model, according to invention principles.

FIG. 10 shows a user interface display image menu supporting a user search for an organization within a particular organization structure model. The search organization function is used to locate organizations that may be of a specific type or play one or more roles within the system. The search function may be used to locate an organization for a Master File maintenance function (e.g., to maintain HPO information) or to find an organization to select and associate with a person. If a desired organization is not found, the data used to do the search is returned for use in adding a new organization, based on the security level of the end user. Prompt elements 605–617 in window 600 support user entry of search criteria and action icons 619, 621 and 625 support initiation of a search, clearing the search form and canceling the search respectively. Search criteria may include, for example, an encounter provider role indicator 605, a service provider role indicator 607, a receivable role indicator 609, organization name (full or partial) 611, status 613, organization type 615 (e.g. Business Office, HPO, Administrative Organization). Other search criteria entered via element 617 may specify another organization role (e.g., employer/sponsor), main contact city, maintain contact phone number, and identifier types the organization issues. Search results may identify one or more organizations meeting the criteria.

FIG. 11 shows a composite user interface display image including a first window supporting a user search for an organization within a particular organization structure model in window 700 and a second window 705 showing corresponding search results. Prompt elements 715–723 in window 700 support user entry of search criteria and action icons 725 and 727 support initiation of a search and clearing the search form respectively. Search criteria include criteria described in connection with FIG. 10. This search form is usable to identify candidate organizations for a desired activity such as for patient movement tracking, reporting functions and maintenance and may also be used to schedule activities. Further, upon user selection of an organization in search window 705, characteristics of the selected organization are displayed in window 710.

The systems, processes and user interface forms presented in FIGS. 1–11 are not exclusive. Other systems, processes and user interface forms may be derived in accordance with the principles of the invention to accomplish the same objectives. The inventive principles may be applied in a variety of environments for identifying and tracking organization related information and to facilitate set-up, maintenance and operation of an organization structure and are not constrained to be used in the healthcare field. Specifically, the inventive principles are applicable to manage, track and identify organization information wherever organization structure tracking and complexity pose a burden.

What is claimed is:

1. A method for providing a user interface for maintaining organization related information in support of organization operation, comprising the steps of;
    initiating generation of at least one displayed image including,
        a window presenting image elements representing an encompassing organization structure including a plurality of constituent organizations and searchable to find an organization of a particular type for performing a particular role for a particular patient;
        at least one menu supporting modification of information representing said encompassing structure by at least one of, (a) adding an organization, (b) removing an organization and (c) moving an organization from a first position to a second position in said encompassing organization structure; and
    updating a database to incorporate modifications of said information representing said encompassing organization structure made via said at least one menu in response to user command.

2. A method according to claim 1, wherein
said information representing said encompassing organization structure comprises a first organization profile associated with a date said first profile is valid and including the step of
providing at least one prompt element supporting user selection of said first profile from a plurality of profiles with associated respective different dates of validity.

3. A method according to claim 1, wherein
said information representing said encompassing organization structure comprises a first profile and
said at least one displayed image supports a user in establishing a second profile by incorporating data from said first profile, said second profile comprising information identifying a second encompassing organization structure derived by modifying said information from said first profile.

4. A method for providing a user interface for maintaining organization related information in support of organization operation, comprising the steps of:
    in at least one displayed image, initiating display of a first image window presenting image elements representing an encompassing organization structure including a plurality of constituent organizations and searchable to find an organization of a particular type for performing a particular role for a particular patient;
    initiating display of a second image window supporting modification of information representing said encompassing organization structure by at least one of, (a) adding an organization, (b) removing an organization and (c) moving an organization from a first position to a second position in said encompassing organization structure; and
    initiating display of a third image window supporting user editing of characteristics of a constituent organization in said encompassing organization structure in response to user selection of at least one image element in a displayed image window.

5. A method according to claim 4, including the step of
updating a database to incorporate modifications of said information representing said encompassing organization structure made via said at least one displayed image in response to user command.

6. A method according to claim 4, including the step of
said first, second and third image windows are presented as overlay images in a common single window in a display image.

7. A method according to claim 4, wherein
said encompassing organization structure comprises a hierarchical organization of constituent organizations with an associated dare of validity of said structure.

8. A method according to claim 4, wherein
said characteristics of said constituent organization include at least one of, (a) organization type identification information, (b) organization role identification information, (c) organization type identification information and (d) organization contact information.

9. A method according to claim 8, wherein
said constituent organization type identifies an organization type comprising at least one of, (a) a health care provider organization, (b) a health care payer organization, (c) a health care administration organization and (d) a business organization.

10. A method according to claim 8, wherein
said constituent organization role identifies an organizational relationship comprising at least one of, (a) a relationship between an individual involved in health care delivery and a health care service provider, (b) a relationship between a creditor and a business organization and (c) a relationship between a health care service provider and an organization including a location for hosting a patient encounter with a healthcare enterprise involving patient and healthcare enterprise interaction.

11. A method according to claim 8, wherein
said constituent organization role identifies an organizational role comprising at least one of, (a) an employer, (b) an issuer of identifiers for identifying items associated with a person, (c) a payment guarantor, (d) a creditor, (e) a service provider and (f) an organization hosting a patient encounter with a healthcare enterprise involving patient and healthcare enterprise interaction.

12. A method according to claim 8, wherein
said characteristics of said constituent organization include a constituent organization legal name and an alias name.

13. A method according to claim 8, wherein
said constituent organization contact information comprises at least one of, (a) contact name, (b) contact address, (c) contact phone number and (d) contact Email address.

14. A method according to claim 8, wherein
said constituent organization contact information includes a template set of contact types prompting contact information to be incorporated for at least one of, (a) authorization, (b) claim submission, (c) claim inquiry, (d) billing, (e) benefits inquiry, (f) contract information and (g) guarantor information.

* * * * *